United States Patent [19]

Forestiere et al.

[11] Patent Number: 5,668,293

[45] Date of Patent: Sep. 16, 1997

[54] CATALYST AND A BENZENE HYDROGENATION PROCESS USING SAID CATALYST

[75] Inventors: Alain Forestiere, Vernaison; Pierre Yout, Vienne; Henri Delhomme, Sainte Foy les Lyrons, all of France

[73] Assignee: Institut Francais du Petrole, Rueil Malmaison, France

[21] Appl. No.: 392,359

[22] Filed: Feb. 16, 1995

[30] Foreign Application Priority Data

Feb. 17, 1994 [FR] France ................... 94 01916

[51] Int. Cl.$^6$ ................... C07C 5/10
[52] U.S. Cl. ................... 585/269; 585/270; 502/170; 502/171
[58] Field of Search ................... 502/150, 170, 502/171, 330; 585/269, 270, 207

[56] References Cited

U.S. PATENT DOCUMENTS

| | | | |
|---|---|---|---|
| 3,531,448 | 9/1970 | Johnson ................... | 585/207 |
| 3,591,649 | 7/1971 | Kroll et al. ................... | 585/270 |
| 3,840,608 | 10/1974 | Suggitt et al. ................... | 260/667 |
| 4,357,478 | 11/1982 | Hillion et al. ................... | 568/816 |

OTHER PUBLICATIONS

Chemical Abstracts, vol. 113, No. 23 (211547y), Dec. 3, 1990, p. 722.

*Primary Examiner*—Glenn A. Caldarola
*Attorney, Agent, or Firm*—Millen, White, Zelano & Branigan, P.C.

[57] ABSTRACT

The invention concerns a process and catalyst for the production of cyclohexane by hydrogenation of benzene, comprising at least the two following steps: a) gradually introducing the feed of benzene for hydrogenation and a hydrogen-rich gas into a reaction zone containing a cyclohexane-rich liquid and a nickel-based catalyst in colloidal suspension and recovering a gaseous phase containing cyclohexane, hydrogen and benzene; b) introducing the gaseous phase into a reactor operating under hydrogenation conditions and containing at least one fixed bed of a solid nickel-based hydrogenation catalyst, wherein the nickel-based catalyst used in step a) is a product which results from the reduction, by at least one trialkylaluminium compound, of a solution of at least one nickel carboxylate and at least one sodium carboxylate in solution, the Ni:Na molar ratio being between 2:1 and 1000:1 in a hydrocarbon or a hydrocarbon mixture.

21 Claims, 1 Drawing Sheet

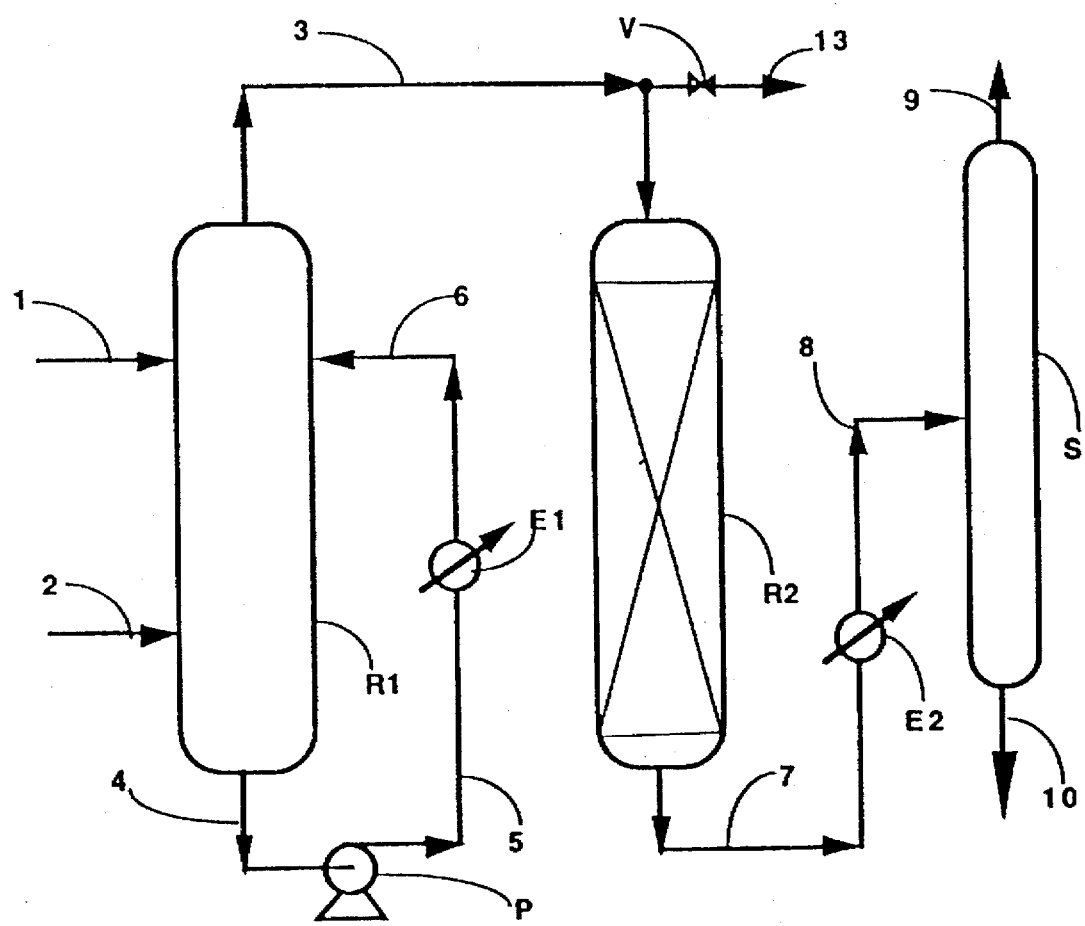

CATALYST AND A BENZENE HYDROGENATION PROCESS USING SAID CATALYST

BACKGROUND OF THE INVENTION

The present invention concerns a homogeneous nickel-based catalyst particularly for use in the hydrogenation of benzene.

The present invention also concerns a process for the production of cyclohexane by benzene hydrogenation, which is carried out in at least two steps. During the first step, benzene hydrogenation is effected in the liquid phase in the presence of a colloidal suspension of a nickel-based catalyst and at a pressure and temperature which enables a vapour phase to be recovered which contains at least a portion of the cyclohexane formed. During the second step, the vapour phase obtained in the first step is sent to a zone, termed the finishing hydrogenation zone, in which the products which can be hydrogenated contained in this vapour phase are hydrogenated in the presence of a solid catalyst.

Hydrogenation of benzene to cyclohexane is a highly exothermic reaction and is thus favoured by low temperatures and high partial pressures of hydrogen. A number of industrial processes have been developed and can be differentiated by their operational conditions, which depend on whether the reaction is carried out in the liquid or the vapour phase. These processes are also differentiated by the nature of the catalyst and the method used to compensate for the temperature rise due to the exothermicity of the reaction.

Among the most well known processes which use the liquid phase are the Hydrar process developed by Union Oil Product which uses a fixed platinum-based catalyst bed. In this process, the benzene feed and a cyclohexane recycle, mixed with fresh hydrogen or recycled hydrogen after recompression to the required pressure, are preheated then introduced into a series of two or three reactors in which the temperatures are stepped up between 200° C. and 300° C. and which operate at about 3 megapascals (MPa). Practically complete conversion per pass is achieved. The effluent from the reactors is cooled by heat exchange with the feed and a portion of the liquid is returned as the diluent to facilitate temperature control. The Houdry process uses three reactors in series operating with fixed beds with cyclohexane recycling. The Sinclair-Engelhard process uses a single reactor from which heat is eliminated in situ using a bank of tubes to produce vapour, and in which cyclohexane is not recycled. In the BP process, hydrogenation is carried out in two successive steps. In this process, the effluent from the first step contains about 95% by weight of cyclohexane and the reaction temperature is controlled by recycling liquid and vapour. In this process, temperature control using both the sensible heat energy and heat of evaporation of the recycled cyclohexane means that the recirculation ratio is substantially reduced, but the partial pressure of hydrogen is also reduced which means that a second, finishing, reactor must be used to complete the hydrogenation. Finally, in the Institut Francais du Petrole (IFP) process, the reaction is carried out in the liquid phase at a temperature of about 185° C. at a pressure of 2 to 3.5 MPa in the presence of a nickel-based catalyst which is held in suspension by agitation using an external circuit. The hydrogenated product leaves the reactor in the vapour phase, helping to remove some of the heat. The rest of the heat given out by the reaction is recovered in an exchanger located in the external circuit (circulation of the stirring liquid phase) and used to produce low pressure vapour. The main drawback with this process is due to the fact that the catalyst used is a nickel which is pyrophoric to a greater or lesser extent, in which the colloidal particles are relatively large and which limits both activity and the stability of the suspension.

In order to use or sell cyclohexane today, a very pure product must be produced containing less than 500 ppm of total impurities. In particular, the majority of industrialised countries have imposed standards requiring the benzene content to be below about 100 ppm. These criteria mean that a relatively low temperature must be used (for example, less than about 300° C.) along with a catalyst which does not favour either isomerisation of the cyclohexane to methylcyclopentane or hydrocracking. When a nickel-based catalyst is used, isomerisation only occurs above 250° C.

SUMMARY OF THE INVENTION

We have unexpectedly discovered a process for the production of cyclohexane by hydrogenation of benzene which can satisfy the specifications required for the cyclohexane produced. This process uses a nickel-based catalyst in its first step which is more active and more stable than that used in the process described in U.S. Pat. No. 4,357,478.

The present invention thus concerns a process for the production of cyclohexane by hydrogenation of benzene, comprising at least two, preferably successive, steps as follows:

a) gradually introducing the feed of benzene for hydrogenation and a hydrogen-rich gas into a reaction zone containing a cyclohexane-rich liquid phase and a nickel-based catalyst in suspension in said phase, said reaction zone being maintained at a temperature of about 100° C. to about 250° C., at an absolute pressure of about 0.5 MPa to about 10 MPa, and recovering a gaseous phase containing cyclohexane, hydrogen and benzene, b) introducing the gaseous phase obtained from step a) into a reactor containing at least one fixed bed of a solid nickel-based hydrogenation catalyst, said reactor being maintained at a temperature of about 100° C. to about 300° C., at an absolute pressure of about 0.5 MPa to about 10 MPa, the hourly space velocity being between 1 $h^{-1}$ and 10 $h^{-1}$, and recovering substantially pure cyclohexane after depressurizing and cooling, said process being characterised in that the nickel-based catalyst used in step a) is produced using at least one trialkylaluminium with formula $AlR^1R^2R^3$, where $R^1$, $R^2$ and $R^3$ each independently represent a linear or branched alkyl group containing 1 to 12 carbon atoms, most preferably 1 to 4 carbon atoms, to reduce a solution, in a hydrocarbon or hydrocarbon mixture, of at least one nickel carboxylate with formula $R^4COONi$, where $R^4$ is a hydrocarbon residue containing 1 to 24 carbon atoms, most preferably 6 to 12 carbon atoms, and at least one sodium carboxylate with formula $R^5COONa$ where $R^5$ is a hydrocarbon residue containing 1 to 24 carbon atoms, preferably 6 to 12 carbon atoms, the Ni:Na molar ratio being between 2:1 and 1000:1, preferably between 2:1 and 500:1, $R^4$ and $R^5$ normally being constituted by hydrocarbon residues, preferably linear or branched alkyl groups.

The nickel and sodium salts are normally used in solution in a hydrocarbon or hydrocarbon mixture with an initial boiling point of more than 100° C., preferably more than 140° C. and most preferably at least 160° C. Preferably, a mixture formed by a saturated hydrocarbon cut and cyclohexane is used.

The solution used in step a) most often contains at least 30% by weight of cyclohexane, preferably at least 40% by weight of cyclohexane and most preferably at least 50% by weight of cyclohexane with respect to the total weight of the cyclohexane and the hydrocarbon cut used.

The present invention also concerns a nickel-based catalyst, in particular for use in a process for the production of cyclohexane, formed by a suspension, in a hydrocarbon or mixture of hydrocarbons produced by using at least one trialkylaluminium with formula $AlR^1R^2R^3$ where $R^1$, $R^2$ and $R^3$ have the meanings given above, to reduce a solution, in a hydrocarbon or hydrocarbon mixture, of at least one nickel carboxylate with formula $R^4COONi$, where $R^4$ has the meaning given above, and at least one sodium carboxylate with formula $R^5COONa$ where $R^5$ has the definition given above, the Ni:Na molar ratio being between 2:1 and 1000:1, preferably between 2:1 and 500:1. In general, the suspension is in a hydrocarbon mixture which preferably includes cyclohexane in the proportions indicated above for the solution in step a) of the process.

The trialkylaluminium used is most preferably either triethylaluminium of triisobutylaluminium. The nickel and sodium carboxylates used are generally derivatives of aliphatic carboxylic acids. Most preferably, a nickel carboxylate and a sodium carboxylate are used which derive from the same carboxylic acid. The nickel compound used is generally a nickel octoate such as nickel 2-ethylhexanoate, and the sodium compound is also an octanoate, for example sodium 2-ethylhexanoate. These salts are generally reduced at substantially atmospheric pressure, at a temperature which is less than or equal to the boiling point of cyclohexane. Excess trialkylaluminium is normally used. The molar ratio of aluminium over the sum of the nickel plus the sodium is generally 1.1:1 to 10:1, preferably 1.5:1 to 4:1. The product of this first step can be made more active in a subsequent step which consists of heating the suspension to a temperature above about 100° C. at a pressure above atmospheric pressure, for example to a temperature of about 175° C. and a pressure of 0.8 MPa. The heating period is sufficient to improve the activity of the catalyst, at least one hour, for example two hours. After cooling, the reduced nickel-based catalyst is in the form of a black colloidal suspension in cyclohexane. This non abrasive colloidal suspension, which can be pumped, is generally used as it is in the first step of the process of the invention. The quantities of nickel salts and sodium salts used are normally selected so that the final concentration of nickel in solution in the cyclohexane is about 1% to about 10% by weight, most frequently about 2% to about 8% by weight, and the sodium concentration of the solution is about 0.02% by weight to about 5% by weight, most frequently about 0.04% to about 2%.

A finishing reactor treats the untransformed gaseous effluent to ensure the reliability and quality. A practically stoichiometric yield is obtained and the purity of the product is principally linked to that of the starting benzene.

The gaseous products from the first step are generally sent directly to the second step in which hydrogenation, termed finishing hydrogenation, is carried out in a reactor containing at least one fixed bed of a solid nickel-based hydrogenation catalyst. This hydrogenation is carried out in the vapour phase in the presence of the catalyst which is preferably deposited on a solid support such as an alumina or silica based support. The solid catalyst contains nickel which is preferably in its oxidized form. The use of a catalyst containing nickel in its oxidized form greatly reduces the risk of pentane, hexane or methycyclopentane formation from the benzene still present in the vapour phase leaving step a). The catalyst preferably contains at least 60% by weight, most preferably 75% to 95% by weight of the total nickel present in the oxide form. The nickel oxide can be present in a proportion of 1% to 50% by weight with respect to the total weight of the catalyst. The oxidized phase and the metallic phase can be measured by X ray diffraction or by chemisorption of hydrogen on the metallic phase present.

The solid catalyst from step b) can be prepared using any conventional method known to the skilled person. This catalyst can thus be prepared by impregnation, mixing, or coprecipitation of the precursor salts used with the support used. The catalyst may be pretreated with hydrogen at low temperature, for example between 150° C. and 300° C., to produce the catalytic form desired and in particular the desired oxide content.

EXAMPLE 1 (COMPARATIVE)

10 litres (7.79 kg) of pure cyclohexane was mixed with 7.34 kg of a solution $S_1$ of nickel octoate containing 13% by weight of nickel. Solution $S_1$ was a solution of nickel octoate in a saturated hydrocarbon cut with an initial boiling point above 160° C., containing less than 1% of water. After mixing, 15.13 kg of a solution $S_2$ containing 0.954 kg (16.3 moles) of nickel was obtained.

6.21 kg (54.5 moles) of triethylaluminium was introduced into a stainless steel reactor equipped with an efficient stirring system and a high performance cooling system, followed by solution $S_2$, at atmospheric pressure and controlling the temperature and the flow of the effluent gas.

The rate of addition of solution $S_2$ was regulated to keep the temperature of the reaction medium at the boiling point of the cyclohexane under the selected pressure conditions. The Al/Ni molar ratio was 3.4. The addition period was two hours. When addition was finished, the resulting mixture was brought to 180° C. for a further two hours at a controlled pressure of 0.8 MPa to activate the catalyst.

Following cooling and returning to atmospheric pressure, 15.9 kg of a colloidal suspension of catalyst was recovered in which the nickel content was 6% by weight and the aluminium content was 9.25% by weight.

A portion of this catalytic suspension was used to continuously hydrogenate benzene in a small pilot unit which is schematically shown in the accompanying FIGURE.

100 g (6 g, or 0.1 mole, of nickel), of the catalytic suspension was introduced into reactor $R_1$ in which the cyclohexane was already present at a predetermined level (80% of the volume of the reactor). The contents of the reactor were then preheated with stirring (by circulating a liquid by pump P) to 180° C. at a hydrogen pressure of 3 MPa.

Benzene was then introduced via line 1 (in which the sulphur content was 0.2 ppm by weight and the water content was 50 ppm by weight), at a flow rate of 108 grammes per hour (g/h), i.e., a molar flow rate of 1.38 moles per hour.

At the same time, a gas containing 95% by volume of hydrogen, 4.80% by volume of C1 to C5 hydrocarbons and 0.2% by volume of nitrogen was introduced at a flow rate of 105 litres per hour (l/h), corresponding to a molar flow rate of about 4.2 moles/h of hydrogen. The hydrogen/benzene molar ratio was thus about 3.04:1.

The liquid recovered from the bottom of reactor R1 via line 4 was pumped by pump P via line 5 to heat exchanger E1 and returned to reactor R1 via line 6. During hydrogenation, reactor R1 was maintained at a temperature of about 180° C. and the pressure at 3 MPa. The vapour phase containing hydrogen, a little unconverted benzene and cyclohexane, was sent via line 3 to finishing reactor R2 which contained a solid nickel-based catalyst. This catalyst had been prepared by impregnating alumina spherules with a specific surface area of 250 m²/g and a total pore volume of 0.65 cm³/g with nickel nitrate followed by drying and calcining at 300° C. for 6 hours. The nickel content of the catalyst was 15% by weight. Before using it in reactor R2 to hydrogenate the gaseous phase from reactor R1, this catalyst was treated with hydrogen at 250° C. for 15 hours at a pressure of 0.2 MPa and a flow rate of 800 litres/litre of catalyst. During hydrogenation of the gaseous phase from reactor R1 arriving via line 3, reactor R2 operated under the following conditions:

Partial pressure of hydrogen: 0.6 MPa
VVH (hourly space velocity) 2
Inlet temperature 180° C.
Maximum temperature in reactor 240° C.

The effluent from reactor R2 was sent via line 7 to heat exchanger E2 where it was cooled, then via line 8 to a high pressure separating column to separate the gaseous phase which was recovered via line 9, and a liquid phase formed by very pure cyclohexane which was recovered via line 10. The benzene used during this test was a high purity benzene characterised by a crystallisation point of 5.5° C., corresponding to a total impurity content of the order of 400 ppm, of which 280 ppm were saturate C6 and C7 hydrocarbons, 100 ppm was cyclohexane and 20 ppm was toluene. A small amount of the vapour phase leaving reactor R1 via line 3 was intermittently removed via line 13, for analysis, by opening valve V. This fraction was cooled and a liquid phase containing cyclohexane and benzene was separated from a gaseous phase containing mainly hydrogen. During the first 15 days of operation, the cyclohexane purity was excellent and remained above 99%. After 2 months of operation, the cyclohexane leaving reactor R1 via line 3 contained about 1000 ppm of benzene. The benzene content in the cyclohexane recovered via line 10 was permanently below 30 ppm throughout the test period. The cyclohexane recovered via line 10 after 2 months of testing had a crystallisation point of 6.40° C. The cyclohexane recovered contained 5 ppm by weight of saturated C5 hydrocarbons and 300 ppm of saturated C6 and C7 hydrocarbons, of which 20 ppm was methylcyclopentane.

EXAMPLE 2

Example 1 was repeated using a catalyst containing 600 ppm of sodium in reactor R1, obtained as follows.

10 litres (7.79 kg) of pure cyclohexane was mixed with 7.34 kg of a solution $S_1$ of nickel octoate containing 13% by weight of nickel and 80 grammes of a solution $S_3$ containing 12% by weight of sodium. Solution $S_1$ was a solution of nickel octoate in a saturated hydrocarbon cut with an initial boiling point above 160° C., containing less than 1% of water. Solution $S_3$ was a solution of sodium octoate in a saturated hydrocarbon cut, with an initial boiling point of more than 160° C., containing less than 1% by weight of water. After mixing, 15.21 kg of a solution $S_4$ containing 0.954 kg (16.3 moles) of nickel and 9.6 grammes (0.42 moles) of sodium was obtained.

6.21 kg (54.5 moles) of triethylaluminium was introduced into a stainless steel reactor equipped with an efficient stirring system and a high performance cooling system, followed by solution $S_4$, at atmospheric pressure and controlling the temperature and the flow of the effluent gas.

The rate of addition of solution $S_4$ was regulated to keep the temperature of the reaction medium at the boiling point of the cyclohexane under the selected pressure conditions. The Al/Ni molar ratio was 3.4. The Ni/Na molar ratio was 38.7. The addition period was two hours. When addition was finished, the resulting mixture was brought to 180° C. for a further two hours at a controlled pressure of 0.8 MPa to activate the catalyst.

Following cooling and returning to atmospheric pressure, 16 kg of a colloidal suspension of catalyst was recovered in which the nickel content was 6% by weight, the aluminium content was 9.25% by weight and the sodium content was 600 ppm by weight.

A portion of this catalytic suspension was used to continuously hydrogenate benzene in a small pilot unit which is schematically shown in the accompanying FIGURE.

100 g (6 g, or 0.1 mole, of nickel and 0.06 grammes, or 0.0023 moles, of sodium), of the catalytic suspension was introduced into reactor $R_1$ in which the cyclohexane was already present at a predetermined level (80% of the volume of the reactor). The contents of the reactor were then preheated with stirring (by circulating a liquid by pump P) to 180° C. at a hydrogen pressure of 3 MPa.

Benzene was then introduced via line 1 (in which the sulphur content was 0.2 ppm by weight and the water content was 50 ppm by weight), at a flow rate of 108 grammes per hour (g/h), i.e., a molar flow rate of 1.38 moles per hour. Reduction was carried out under the same conditions as those described for Example 1. After 2 months of operation, the cyclohexane leaving reactor R1 via line 3 contained less than 200 ppm of benzene. The benzene concentration in the cyclohexane recovered via line 10 remained below 10 ppm for the entire test period. The cyclohexane recovered via line 10 after 2 months of testing had a crystallisation point of 6.46° C. The recovered cyclohexane contained 290 ppm of saturated C6 and C7 hydrocarbons, 10 ppm of which was methylcyclopentane.

EXAMPLE 3

Example 1 was repeated using a catalyst containing 1% by weight of sodium in reactor R1, obtained as follows.

10 litres (7.79 kg) of pure cyclohexane was mixed with 7.34 kg of a solution $S_1$ of nickel octoate containing 13% by weight of nickel and 1.37 kg of a solution $S_3$ containing 12% by weight of sodium. Solution $S_1$ was a solution of nickel octoate in a saturated hydrocarbon cut with an initial boiling point of more than 160° C., containing less than 1% of water. Solution $S_3$ was a solution of sodium octoate in a saturated hydrocarbon cut, with an initial boiling point of more than 160° C., containing less than 1% by weight of water. After mixing, 16.5 kg of a solution $S_5$ containing 0.954 kg (16.3 moles) of nickel and 0.164 kg (7.13 moles) of sodium was obtained.

6.21 kg (54.5 moles) of triethylaluminium was introduced into a stainless steel reactor equipped with an efficient stirring system and a high performance cooling system, followed by solution $S_5$, at atmospheric pressure and controlling the temperature and the flow of the effluent gas.

The rate of addition of solution $S_5$ was regulated to keep the temperature of the reaction medium at the boiling point of the cyclohexane under the selected pressure conditions. The Al/Ni molar ratio was 3.4. The Ni/Na molar ratio was 2.3. The addition period was two hours. When addition was finished, the resulting mixture was brought to 180° C. for a further two hours at a controlled pressure of 0.8 MPa to activate the catalyst.

Following cooling and returning to atmospheric pressure, 17 kg of a colloidal suspension of catalyst was recovered in which the nickel content was 5.6% by weight, the aluminium content was 8.7% by weight and the sodium content was 0.96% by weight.

A portion of this catalytic suspension was used to continuously hydrogenate benzene in a small pilot unit which is schematically shown in the accompanying FIGURE.

100 g (5.6 g, or 0.095 mole, of nickel and 0.96 grammes, or 0.042 moles, of sodium), of the catalytic suspension was introduced into reactor $R_1$ in which the cyclohexane was already present at a predetermined level (80% of the volume of the reactor). The contents of the reactor were then preheated with stirring (by circulating a liquid by pump P) to 180° C. at a hydrogen pressure of 3 MPa.

Benzene was then introduced via line 1 (in which the sulphur content was 0.2 ppm by weight and the water content was 50 ppm by weight), at a flow rate of 108 grammes per hour (g/h), i.e., a molar flow rate of 1.38 moles per hour. Reduction was carried out under the same conditions as those described for Example 1. After 2 months of operation, the cyclohexane leaving reactor R1 via line 3 contained less than 100 ppm of benzene. The benzene concentration in the cyclohexane recovered via line 10 remained below 10 ppm for the entire test period. The cyclohexane recovered via line 10 after 2 months of testing had a crystallisation point of 6.50° C. The recovered cyclohexane contained 280 ppm of saturated C6 and C7 hydrocarbons, and did not contain a detectable quantity of methylcyclopentane.

We claim:

1. A process for the production of cyclohexane by hydrogenation of benzene, comprising at least two steps, as follows:
   a) gradually introducing the feed of benzene for hydrogenation and a hydrogen-rich gas into a reaction zone containing a cyclohexane-rich liquid phase and a nickel-based catalyst in suspension in said phase, said reaction zone being maintained at a temperature of about 100° C. to about 250° C., at an absolute pressure of about 0.5 MPa to about 10 MPa, and recovering a gaseous phase containing cyclohexane, hydrogen and benzene,
   b) introducing the gaseous phase obtained from step a) into a reactor containing at least one fixed bed of a solid nickel-based hydrogenation catalyst, said reactor being maintained at a temperature of about 100° C. to about 300° C., at an absolute pressure of about 0.5 MPa to about 10 MPa, the hourly space velocity being between 1 $h^{-1}$ and 10 $h^{-1}$, and recovering substantially pure cyclohexane after depressurizing and cooling, said process being characterised in that the nickel-based catalyst in suspension used in step a) is produced using at least one trialkylaluminium with formula $AlR^1R^2R^3$ where $R^1$, $R^2$ and $R^3$ each independently represent a linear or branched alkyl group containing 1 to 12 carbon atoms, to reduce a solution, in a hydrocarbon or hydrocarbon mixture, of at least one nickel carboxylate with formula $R^4COONi$, where $R^4$ is a hydrocarbon residue containing 1 to 24 carbon atoms, and at least one sodium carboxylate with formula $R^5COONa$ where $R^5$ is a hydrocarbon residue containing 1 to 24 carbon atoms, the Ni:Na molar ratio being between 2:1 and 1000:1.

2. A process according to claim 1, wherein the $R^1$, $R^2$ and $R^3$ each independently represents a linear or branched alkyl group containing 1 to 4 carbon atoms, $R^4$ is a hydrocarbon residue containing 6 to 12 carbon atoms, and $R^5$ is a hydrocarbon residue containing 6 to 12 carbon atoms.

3. A process according to claim 1, wherein the trialkylaluminium used is triethylaluminium or triisobutylaluminium.

4. A process according to claim 1, wherein the nickel and sodium carboxylates are salts of aliphatic carboxylic acids.

5. A process according to claim 4, wherein the nickel and sodium carboxylates are salts of the same carboxylic acid.

6. A process according to claim 1, wherein the nickel and sodium carboxylates are used in solution in a hydrocarbon or hydrocarbon mixture with an initial boiling point of more than 100° C.

7. A process according to claim 6, wherein the nickel and sodium carboxylates are used in solution in a mixture formed by a saturated hydrocarbon cut and cyclohexane.

8. A process according to claim 1, wherein the quantity of trialkylaluminium used is such that the molar ratio of aluminium to the sum of the nickel and sodium is 1.1:1 to 10:1 and in which after the first reduction step for the nickel salt by the aluminium compound, the suspension is heated to a temperature above about 100° C. at a pressure above atmospheric pressure for a period sufficient to increase the activity of the catalyst.

9. A suspension of a nickel-based catalyst in a hydrocarbon or hydrocarbon mixture, produced by using at least one trialkylaluminium of the formula $AlR^1R^2R^3$ where $R^1$, $R^2$ and $R^3$ each independently represent a linear or branched alkyl group containing 1 to 12 carbon atoms, to reduce a solution, in a hydrocarbon or hydrocarbon mixture, of at least one nickel carboxylate of the formula $R^4COONi$, where $R^4$ is a hydrocarbon residue containing 1 to 24 carbon atoms, and at least one sodium carboxylate of the formula $R^5COONa$ where $R^5$ is a hydrocarbon residue containing 1 to 24 carbon atoms, the Ni:Na molar ratio being between 2:1 and 1000:1.

10. A suspension according to claim 9, wherein $R^1$, $R^2$ and $R^3$ each independently represents a linear or branched alkyl group containing 1 to 4 carbon atoms, $R^4$ is a hydrocarbon residue containing 6 to 12 carbon atoms, and $R^5$ is a hydrocarbon residue containing 6 to 12 carbon atoms.

11. A suspension according to claim 9, wherein the trialkylaluminium used is triethylaluminium or triisobutylaluminium.

12. A suspension according to claim 9, wherein the nickel and sodium carboxylates are salts of aliphatic carboxylic acids.

13. A suspension according to claim 12, wherein the nickel and sodium carboxylates derive from the same carboxylic acid.

14. A suspension according to claim 9, wherein the nickel and sodium carboxylates are used in solution in a hydrocarbon or hydrocarbon mixture with an initial boiling point of more than 100° C.

15. A suspension according to claim 14, wherein the nickel and sodium carboxylates are used in solution in a mixture formed by a saturated hydrocarbon cut and cyclohexane.

16. A suspension according to any one of claim 9, wherein the quantity of trialkylaluminium used is such that the molar ratio of aluminium to the sum of the nickel and sodium is 1.1:1 to 10:1 and in which after the first reduction step for the nickel salt by the aluminium compound, the suspension is heated to a temperature above about 100° C. at a pressure above atmospheric pressure for a period sufficient to increase the activity of the catalyst.

17. A suspension according to claim 9, wherein the Ni:Na molar ratio is between 2:1 and 500:1.

18. A process according to claim 1, wherein the Ni:Na molar ratio is between 2:1 and 500:1.

19. A suspension according to claim 9, wherein the Ni:Na molar ratio is between 2:1 and 50:1.

20. A process according to claim 1, wherein the Ni:Na molar ratio is between 2:1 and 50:1.

21. A suspension according to claim 9 which is black colloidal suspension.

* * * * *